United States Patent [19]

Siegel et al.

[11] Patent Number: 5,214,207

[45] Date of Patent: May 25, 1993

[54] PHENYL- OR NAPHTHYLAZOBENZENES WITH MULTIPLE REACTIVE GROUPS AND INTERMEDIATES THEREFOR

[75] Inventors: Bernd Siegel, Ludwigshafen; Manfred Patsch, Wachenheim, both of Fed. Rep. of Germany

[73] Assignee: BASF Aktiengesellschaft, Ludwigshafen, Fed. Rep. of Germany

[21] Appl. No.: 753,392

[22] Filed: Aug. 30, 1991

Related U.S. Application Data

[62] Division of Ser. No. 608,842, Nov. 5, 1990, Pat. No. 5,091,516.

[30] Foreign Application Priority Data

Nov. 28, 1989 [DE] Fed. Rep. of Germany ....... 3939286

[51] Int. Cl.$^5$ .................. C07C 275/06; C07C 275/28
[52] U.S. Cl. ......................................... 564/50; 564/48
[58] Field of Search ........................... 564/50, 49, 48; 534/629, 612

[56] References Cited

U.S. PATENT DOCUMENTS 4,841,028  6/1989  Aeschlimann et al. ............. 534/629

FOREIGN PATENT DOCUMENTS 0174909  3/1986  European Pat. Off. .
0208655  3/1987  European Pat. Off. .

OTHER PUBLICATIONS

Tzikas CA 106: 103811b (abstract only), 1987.

*Primary Examiner*—Richard L. Raymond
*Assistant Examiner*—Shailendra Kumar
*Attorney, Agent, or Firm*—Oblon, Spivak, McClelland, Maier & Neustadt

[57] ABSTRACT

Reactive dyes useful for dyeing or printing hydroxyl-or amino-containing organic substrates which are preparable from phenylenediamine intermediates of the formula

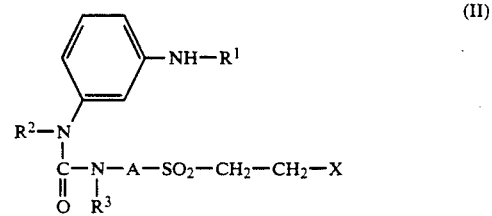

(II)

wherein X is hydroxyl or halogen; $R^1$, $R^2$ and $R^3$ are each hydrogen, $C_1$–$C_4$-alkyl or phenyl; and A is substituted or unsubstituted $C_2$–$C_8$-alkylene.

1 Claim, No Drawings

PHENYL- OR NAPHTHYLAZOBENZENES WITH MULTIPLE REACTIVE GROUPS AND INTERMEDIATES THEREFOR

This is a division of application Ser. No. 07/608,842 filed Nov. 5, 1990 now U.S. Pat. No. 5,091,516.

The present invention relates to novel reactive dyes of the formula I

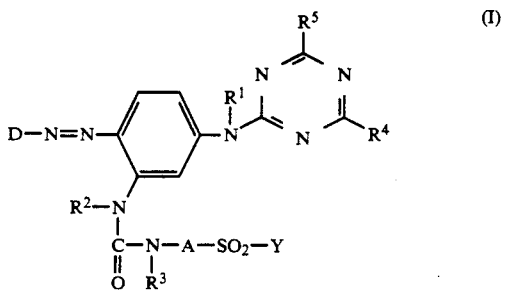

where

R$^1$, R$^2$ and R$^3$ are identical or different and each is independently of the others hydrogen, C$_1$–C$_4$-alkyl or phenyl, R$^4$ is C$_1$–C$_4$-alkoxy, phenoxy or a radical of the formula NL$^1$L$^2$, where L$^1$ and L$^2$ are identical or different and each is independently of the other C$_1$–C$_4$-alkyl, which may be substituted by hydroxyl, hydroxysulfonyl or sulfato, or substituted or unsubstituted phenyl, or L$^1$ and L$^2$ together combine with the nitrogen atom joining them to form a 5- or 6-membered saturated heterocyclic radical which may contain further hetero atoms, or L$^1$ may also be hydrogen, R$^5$ is fluorine, chlorine, bromine, C$_1$–C$_4$-alkylsulfonyl, phenylsulfonyl or a radical of the formula

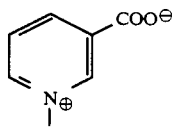

A is C$_2$–C$_8$-alkylene, which may be interrupted by from 1 to 3 oxygen atoms, imino groups or C$_1$–C$_4$-alkylimino groups, Y is vinyl or a radical of the formula —CH$_2$—CH$_2$—Q, where Q is a group which is detachable under alkaline reaction conditions, and D is phenyl or naphthyl, which may each be monosubstituted or polysubstituted by hydroxysulfonyl, carboxyl, C$_1$–C$_4$-alkoxycarbonyl, cyano, C$_1$–C$_4$-alkyl, C$_1$–C$_4$-alkoxy, halogen, nitro or vinylsulfonyl, to novel phenylenediamines as intermediates therefor, and to a method of using the novel dyes for dyeing or printing hydroxyl- or amino-containing fibers.

EP-A-174,909 discloses reactive dyes where the reactive group is a vinylsulfonyl radical which is bonded to the dye moiety via a ureido group.

It is an object of the present invention to provide new reactive dyes which likewise have a vinyl-sulfonyl group bonded to the chromophore by a ureido group but which should have advantageous application properties.

We have found that this object is achieved by the reactive dyes of the formula I defined at the beginning.

Any alkyl or alkylene appearing in the above-mentioned formula I may be either straight-chain or branched.

In substituted phenyl appearing in the above-mentioned formula I, the substituents may be for example, unless otherwise stated, C$_1$–C$_4$-alkyl, C$_1$–C$_4$-haloalkyl, C$_1$–C$_4$-alkoxy, amino, C$_1$–C$_4$-mono- or -dialkylamino, nitro, formyl, cyano, carboxyl and hydroxysulfonyl.

R$^1$, R$^2$ and R$^3$ are each for example methyl, ethyl, propyl, isopropyl, butyl, isobutyl or sec-butyl.

R$^4$ is for example methoxy, ethoxy, propoxy, isopropoxy, butoxy, isobutoxy, sec-butoxy, mono- or dimethylamino, mono- or diethylamino, mono- or dipropylamino, mono- or diisopropylamino, mono- or dibutylamino, N-methyl-N-ethylamino, N-(2-hydroxyethyl)amino, N-(2-hydroxysulfonylethyl)amino, N-(2-sulfatoethyl)amino, mono- or diphenylamino, N-methyl-N-phenylamino, N-ethyl-N-phenylamino, N-propyl-N-phenylamino, N-isopropyl-N-phenylamino, N-butyl-N-phenylamino, 2- or 4-methylphenylamino, N-methyl-N-(2- or 4-methylphenyl)amino, N-ethyl-N-(2- or 4-methylphenyl)amino, 2- or 4-chloromethylphenylamino, N-methyl-N-(2- or 4-chloromethylphenyl)-amino, N-ethyl-N-(2- or 4-chloromethylphenyl)amino, 2- or 4-trifluoromethylphenylamino, N-methyl-N-(2- or 4-trifluoromethylphenyl)amino, N-ethyl-N-(2- or 4-trifluoromethylphenyl)amino, 2-methoxyphenylamino, N-methyl-N-(2-methoxyphenyl)amino, N-ethyl-N-(2-methoxyphenyl)amino,2-aminophenylamino, N-methyl-N-(2-aminophenyl)amino, N-ethyl-N-(2-aminophenyl)amino, 2-methylaminophenylamino, N-methyl-N-(2-methylaminophenyl)amino, N-ethyl-N-(2-methylaminophenyl)amino, 2-dimethylaminophenylamino, N-methyl-N-(2-dimethylaminophenyl)amino, N-ethyl-N-(2-dimethylaminophenyl)amino, 3-nitrophenylamino, N-methyl-N-(3-nitrophenyl)amino, N-ethyl-N-(3-nitrophenyl)amino, 3-cyanophenylamino, N-methyl-N-(3-cyanophenyl)amino, N-ethyl-N-(3-cyanophenylamino), 3-formylphenylamino, N-methyl-N-(3-formylphenyl)amino, N-ethyl-N-(3-formylphenyl)amino, 3-carboxylphenylamino, N-methyl-N-(3-carboxylphenyl)amino, N-ethyl-N-(3-carboxylphenyl)amino, 3-hydroxysulfonylphenylamino, N-methyl-N-(3-hydroxysulfonylphenyl)amino, N-ethyl-N-(3-hydroxysulfonylphenyl)amino, pyrrolidino, piperidino, morpholino, piperazino or N-(C$_1$–C$_4$-alkyl)piperazino.

R$^5$ is for example methylsulfonyl, ethylsulfonyl, propylsulfonyl, isopropylsulfonyl or butylsulfonyl.

A is for example —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —CH(CH$_3$)—CH$_2$—, —CH(CH$_3$)—CH(CH$_3$)—, —(CH$_2$)$_2$—O—(CH$_2$)$_2$—, —(CH$_2$)$_2$—NH—(CH$_2$)$_2$—, —(CH$_2$)—N(CH$_3$)—(CH$_2$)$_2$—, —(CH$_2$)$_2$—O—(CH$_2$)$_2$—O—(CH$_2$)$_2$— or —(CH$_2$)$_2$—O—(CH$_2$)$_2$—O—(CH$_2$)$_2$—O—(CH$_2$)$_2$—.

Y in formula I may inter alia be a group which is detachable under alkaline reaction conditions. Examples of such groups are chlorine, OSO$_3$H, SSO$_3$H, OP(O)(OH)$_2$, C$_1$–C$_4$-alkylsulfonyloxy, substituted or unsubstituted phenylsulfonyloxy, C$_1$–C$_4$-alkanoyloxy, C$_1$–C$_4$-dialkylamino,

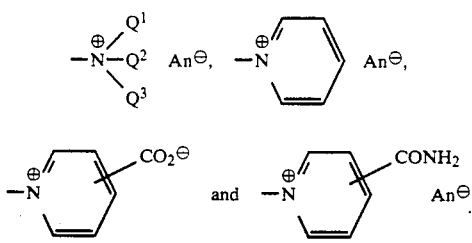

where $Q^1$, $Q^2$ and $Q^3$ are identical or different and each is independently of the others $C_1$-$C_4$-alkyl or benzyl, and $An^\ominus$ is in each case an anion. (Suitable anions are for example fluoride, chloride, bromide, iodide, mono-, di-or trichloroacetate, methylsulfonate, phenylsulfonate and 2- or 4-methylphenylsulfonate.)

D is for example 2,4-dihydroxysulfonylphenyl, 2,5-dihydroxysulfonylphenyl, 2,5-dihydroxysulfonyl-4-methylphenyl, 2,5-dihydroxysulfonyl-6-chlorophenyl, 3,6,8-trihydroxysulfonylnaphth-2-yl, 4,6,8-trihydroxysulfonylnaphth-2-yl, 1,5-dihydroxysulfonylnaphth-2-yl or 1,6-dihydroxysulfonylnaphth-2-yl.

Preference is given to reactive dyes of the formula I in which $R^1$, $R^2$ and $R^3$ are each hydrogen, $R^4$ is a radical of the formula $NL^1L^2$, where $L^1$ is $C_1$-$C_4$-alkyl and $L^2$ is substituted or unsubstituted phenyl, $R^5$ is fluorine or chlorine, A is $C_2$-$C_4$-alkylene, which may be interrupted by an oxygen atom, D is phenyl or naphthyl, which may both be monosubstituted, disubstituted or trisubstituted by hydroxysulfonyl, and Y is as defined above.

Particular preference is given to reactive dyes of the formula I in which $R^4$ is a radical of the formula $NL^1L^2$ where L is $C_1$-$C_4$-alkyl and $L^2$ is phenyl, and D is dihydroxysulfonylphenyl or trihydroxysulfonylnaphthyl.

The novel reactive dyes of the formula I are obtainable in an advantageous manner, for example by conventionally diazotizing an amine of the formula III

D—NH$_2$ (III)

where D is as defined above, and coupling the diazonium salt with a phenylenediamine of the formula II

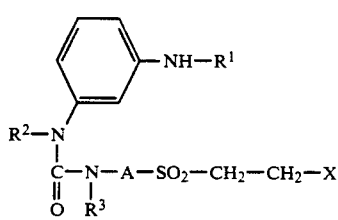

where $R^1$, $R^2$, $R^3$ and A are each as defined above and X is hydroxyl or halogen.

The resulting azo dye of the formula IV

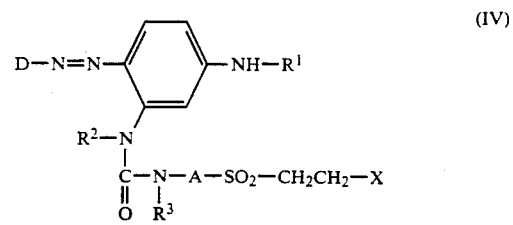

where D, $R^1$, $R^2$, $R^3$, A and X are each as defined above, can then be reacted in a conventional manner with a trihalotriazine and thereafter with a compound of the formula V

$R^4$—H (V)

where $R^4$ is as defined above.

If X is hydroxyl, the final step, which may again be carried out in a conventional manner, is to convert the group —CH$_2$CH$_2$—X into Y (see definition above), for example by esterification with sulfuric acid.

The novel reactive dyes of the formula I are advantageous for dyeing or printing hydroxyl- or amino-containing organic substrates. Such substrates are for example leather and fiber material containing predominantly natural or synthetic polyamides or natural or regenerated cellulose. The novel dyes are preferred for dyeing or printing textile material based on cotton. The reactive dyes according to the present invention can also be used for discharge printing, since they are alkali-dischargeable.

The present invention further provides phenylenediamines of the formula II

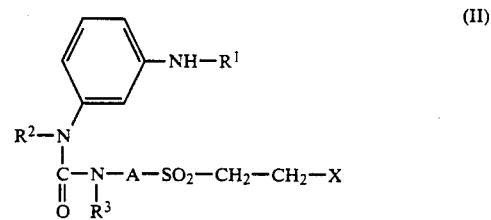

where $R^1$, $R^2$ and $R^3$ are identical or different and each is independently of the other hydrogen, $C_1$-$C_4$-alkyl or phenyl, A is $C_2$—$C_8$-alkylene, which may be interrupted by from 1 to 3 oxygen atoms, imino groups or $C_1$-$C_4$-alkylimino groups, and X is hydroxyl or halogen.

For examples of the definitions, reference should be made to the preceding enumerations.

The novel phenylenediamines of the formula II can be obtained in a conventional manner. For instance, by reacting 3-nitrophenyl isocyanate of the formula VI

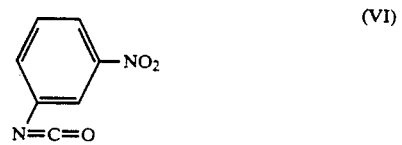

with a sulfur-containing amine of the formula VII

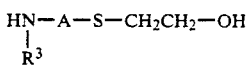 (VII)

where $R^3$ and A are each as defined above, and subjecting the resulting thio compound of the formula VIII

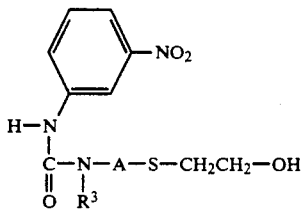 (VIII)

where $R^3$ and A are each as defined above, in a conventional manner first to an oxidation of the thio group to a sulfone group and then to a reduction of the nitro group to an amino group. Thereafter the hydroxyl group can be exchanged for halogen using a conventional halogenating agent (e.g. thionyl chloride, phosphorus trichloride or phosphorus tribromide).

The phenylenediamine derivatives of the formula II according to the present invention are useful intermediates for preparing the novel reactive dyes of the formula I.

The Examples which follow further illustrate the invention. Preparation of intermediates

EXAMPLE 1 a) 82 g (0.5 mol) of 3-nitrophenyl isocyanate in 500 ml of toluene were added dropwise to a solution of 60.5 g (0.5 mol) of 2-amino-2′-hydroxydiethyl sulfide and 200 ml of toluene at 30°–40° C. After the reaction had ended, the solvent was distilled off, and the residue was admixed with 500 ml of water and 1.5 g of sodium tungstate ×2 H$_2$O and oxidized at about 70° C. with 325 g of 30% strength by weight hydrogen peroxide solution. The reaction mixture was subsequently stirred at that temperature for 1.5 hours, then cooled down to about 5° C. and filtered. The filtercake was washed with sodium bisulfite solution and water. This gave 125 g of the compound of the formula

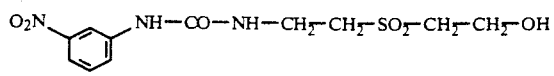

having a melting point of 174°–177° C. (The compound can be recrystallized from glacial acetic acid.)

b) 110 g (0.35 mol) of the compound described in Example 1a) were dissolved in 350 ml of N,N-dimethylformamide, admixed with 3.5 g of palladium on carbon (10% strength by weight), heated to 60° C. and hydrogenated with 23.3 l of hydrogen. The catalyst was then separated off, the solvent was distilled off, and the oily residue was made to crystallize with 100 ml of acetone. This left 80 g of the compound of the formula

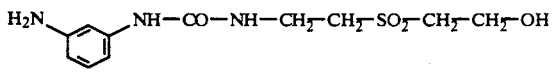

having a melting point of 127°–131° C.

The method of Example 1 was also used to obtain the compounds listed below in Table 1.

TABLE 1

| Example No. | Compound |
|---|---|
| 2 | H$_2$N—C$_6$H$_4$—NH—CO—NH—(CH$_2$)$_3$—SO$_2$—(CH$_2$)$_2$—OH |
| 3 | H$_2$N—C$_6$H$_4$—NH—CO—NH—(CH$_2$)$_2$—O—(CH$_2$)$_2$—SO$_2$—(CH$_2$)$_2$—OH |
| 4 | H$_2$N—C$_6$H$_4$—NH—CO—N(CH$_3$)—(CH$_2$)$_2$—SO$_2$—(CH$_2$)$_2$—OH |

EXAMPLE 5 a) 79.3 g (0.25 mol) of the product described in Example 1a were dissolved in 300 ml of 1,1,1-trichloroethane, admixed with 29.8 g (0.25 mol) of thionyl chloride at 30°–40° C. and heated at the boil until the gas ceased to evolve. Then the solvent and aqueous thionyl chloride were distilled off under reduced pressure, and the residue was recrystallized from glacial acetic acid. This left 44.2 g of the compound of the formula

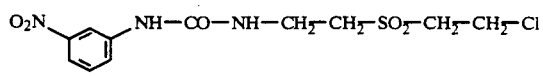

having a melting point of 126°–130° C.

b) 67 g of the product described in Example 5a) were dissolved in 170 ml of N,N-dimethylformamide and hydrogenated with Raney nickel at 60° C. A customary workup gave 47 g of a compound conforming to the formula

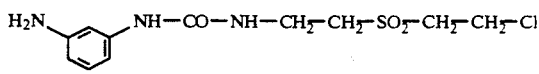

The compounds listed below in Table 2 were obtained similarly to Example 5.

TABLE 2

| Example No. | Compound |
|---|---|
| 6 | 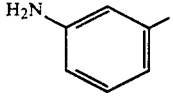 |
| 7 | 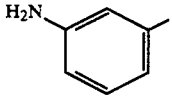 |
| 8 | 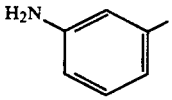 |

Preparation of dyes

EXAMPLE 9

22.1 g (0.1 mol) of aniline-2,4-disulfonic acid were diazotized in 200 ml of water in the presence of hydrochloric acid, and the diazonium salt suspension was added to a solution of 28.7 g (0.1 mol) of the product of Example 1b) in 200 ml of water, the pH of the solution being 3, at 5°–10° C. After the coupling had ended (at pH 5–6), the dye solution was admixed at 0°–5° C. with a suspension of 18.4 g (0.1 mol) of cyanuric chloride and 200 ml of ice-water and warmed to room temperature in the course of 1.5 hours at pH 5–6. After the reaction had ended, the reaction mixture was mixed with 12.5 g (0.1 mol) of N-ethylaniline dissolved in the presence of hydrochloric acid, the pH was maintained at 6–7, and the reaction mixture was heated to 30°–35° C. to complete the condensation. Then the solvent was evaporated and a dye of the formula

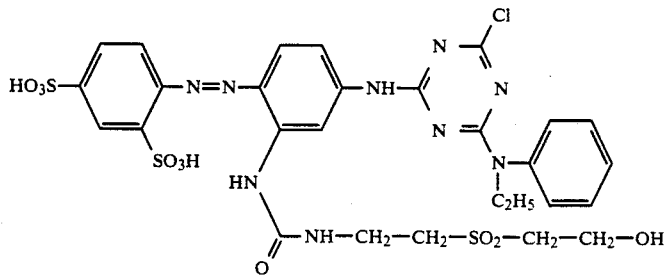

was isolated.

75 g of this dye were added a little at a time to 300 g of sulfuric acid monohydrate at 20°–30° C. The mixture was subsequently stirred at 40° C. for 1.5 hours and then poured onto 1 kg of ice. The resulting reactive dye conforms to the formula

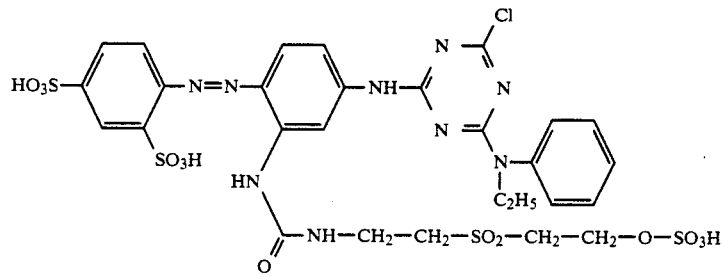

and dyes cotton in a yellowish orange shade having very good light and wet fastness properties.

The same method was used to obtain the dyes of the formula

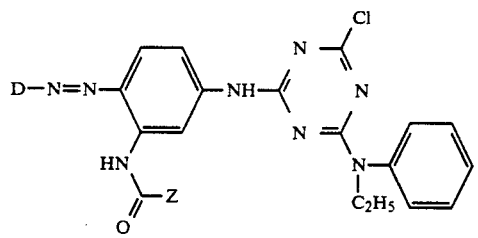

listed in Table 3.

TABLE 3

| Ex. No. | D | Z | Hue on cotton |
|---|---|---|---|
| 10 | 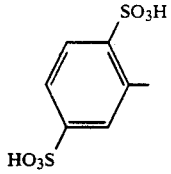 | NH(CH₂)₂—SO₂—(CH₂)₂—O—SO₃H | yellowish orange |
| 11 | 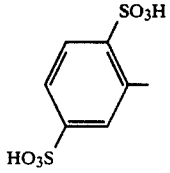 | NH(CH₂)₃—SO₂—(CH₂)₂—O—SO₃H | yellowish orange |
| 12 | 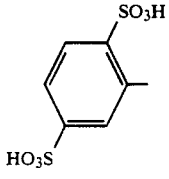 | N(CH₂)₂—SO₂—(CH₂)₂—O—SO₃H<br>\|<br>CH₃ | yellowish orange |
| 13 | 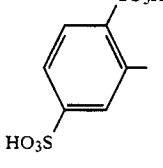 | NH(CH₂)₂—O—(CH₂)₂—SO₂—(CH₂)₂—O—SO₃H | yellowish orange |
| 14 | 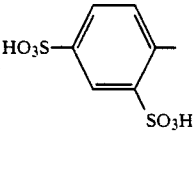 | NH(CH₂)₃—SO₂—(CH₂)₂—O—SO₃H | yellowish orange |
| 15 | 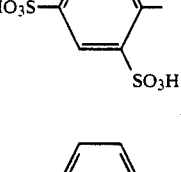 | NH(CH₂)₂—O—(CH₂)₂—SO₂—(CH₂)₂—O—SO₃H | yellowish orange |
| 16 | 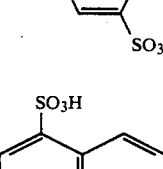 | N—(CH₂)₂—SO₂—(CH₂)₂—O—SO₃H<br>\|<br>CH₃ | yellowish orange |
| 17 | 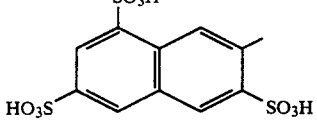 | NH(CH₂)₂—SO₂—(CH₂)₂—O—SO₃H | yellowish orange |
| 18 | 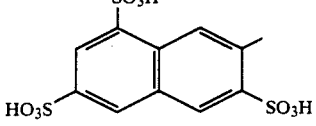 | NH(CH₂)₃—SO₂—(CH₂)₂—O—SO₃H | yellowish orange |

TABLE 3-continued

| Ex. No. | D | Z | Hue on cotton |
|---|---|---|---|
| 19 | 7-methyl-1,3,6-trisulfonaphthalene (SO₃H at 1,6-positions and HO₃S at 3, with methyl) — 1-naphthyl with SO₃H at 1, HO₃S at 6, SO₃H at 3, methyl at 7 | NH(CH₂)₂—O—(CH₂)₂—SO₂—(CH₂)₂—O—SO₃H | yellowish orange |
| 20 | same naphthalene as Ex. 19 | N(CH₃)—(CH₂)₂—SO₂—(CH₂)₂—O—SO₃H | yellowish orange |
| 21 | naphthalene with SO₃H at 1, HO₃S at 3, SO₃H at 5, methyl at 7 | NH(CH₂)₂—SO₂—(CH₂)₂—O—SO₃H | yellowish orange |
| 22 | same naphthalene as Ex. 21 | NH(CH₂)₃—SO₂—(CH₂)₂—O—SO₃H | yellowish orange |
| 23 | same naphthalene as Ex. 21 | NH(CH₂)₂—O—(CH₂)₂—SO₂—(CH₂)₂—O—SO₃H | yellowish orange |
| 24 | same naphthalene as Ex. 21 | N(CH₃)—(CH₂)₂—SO₂—(CH₂)₂—O—SO₃H | yellowish orange |

EXAMPLE 25

22.1 g (0.1 mol) of aniline-2,4-disulfonic acid were diazotized in 200 ml of water in the presence of hydrochloric acid, and the diazonium salt suspension was added to a solution of 28.7 g (0.1 mol) of the product of Example 1b in 250 ml of water, the pH of the solution being 3, at 5°–10° C. After the coupling had ended at pH 5–6, the solvent was evaporated to leave 108.5 g of an electrolyte-containing powder containing the dye of the formula

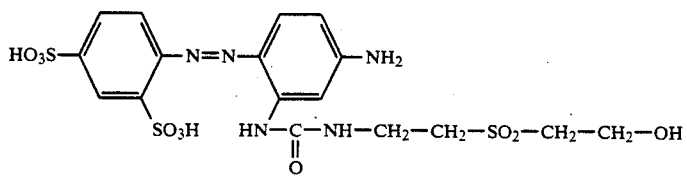

($\lambda_{max}$ = 441 nm)

108 g of this powder were added to 400 g of sulfuric acid monohydrate a little at a time up to an internal temperature of 40° C. and the mixture was stirred at room temperature for about 8 hours. After the reaction had ended, the reaction solution was poured onto 1000 g of ice, the resulting mixture was brought to pH 4–5 with sodium bicarbonate, the precipitated sodium sulfate was separated off, and the filtrate was admixed with a suspension of 18.4 g (0.1 mol) of 1,3,5-trichlorotriazine in 200 ml of ice-water at 0°–5° C. The condensation reaction was carried out at a pH of 5–6 and 5°–10° C. Thereafter the reaction mixture was admixed with 12.5 g (0.1 mol) of N-ethylaniline dissolved in water in the presence of hydrochloric acid, and pH 6 and 20°–30° C. was maintained until the reaction had ended. Potassium chloride was added to isolate a salt-containing dye which, in the form of the free acid, conforms to the formula which, in the form of the free acid, conforms to the formula

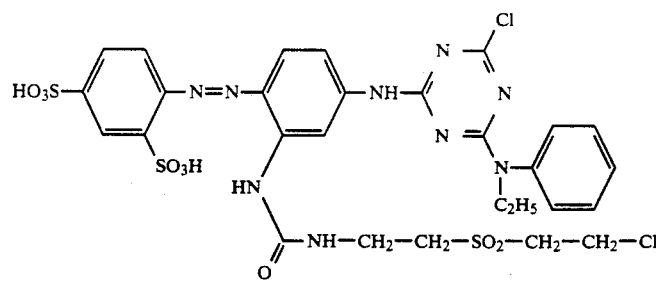

formula

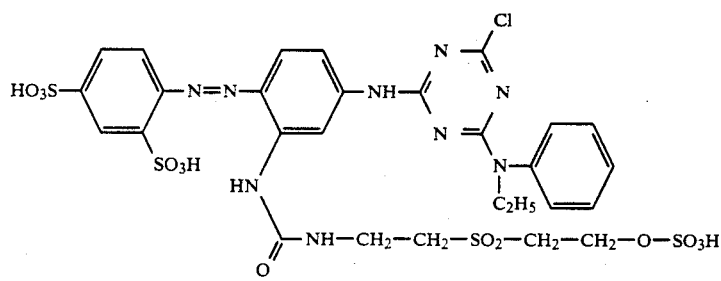

It dyes cellulose fibers in a yellowish orange shade having very good lightfastness properties and good wetfastness properties.

(The compounds listed above in Table 3 can also be prepared by the method of Example 25.)

EXAMPLE 26

22.1 g (0.1 mol) of aniline-2,4-disulfonic acid were diazotized in the presence of hydrochloric acid and coupled with 30.6 g (0.1 mol) of the product of Example 5b) at pH 4-5 and then condensed at 5°-10° C. with 18.4 g (0.1 mol) of cyanuric chloride at pH 5-6. Thereafter the reaction mixture was admixed at 20°-30° C. with 12.5 g (0.1 mol) of N-ethylaniline dissolved in water in the presence of hydrochloric acid and the reaction mixture was maintained at pH 5-6 until the reaction had ended. Potassium chloride was added to salt out a dye It dyes cotton in a yellowish orange shade having good fastness properties.

The method of Example 26 was also used to obtain the dyes of the formula

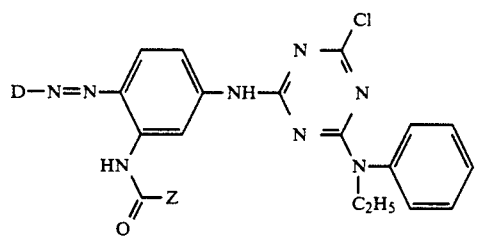

listed in Table 4.

TABLE 4

| Ex. No. | D | Z | Hue on cotton |
| --- | --- | --- | --- |
| 27 | ![SO3H, HO3S substituted benzene] | NH(CH$_2$)$_2$—SO$_2$—(CH$_2$)$_2$—Cl | yellowish orange |
| 28 | ![SO3H, HO3S substituted benzene] | NH(CH$_2$)$_3$—SO$_2$—(CH$_2$)$_2$—Cl | yellowish orange |

TABLE 4-continued

| Ex. No. | D | Z | Hue on cotton |
|---|---|---|---|
| 29 | 2,5-disulfo-4-methylphenyl (SO3H at 1, HO3S at 4-position pattern shown) | N(CH3)(CH2)2—SO2—(CH2)2—Cl | yellowish orange |
| 30 | 2,5-disulfo-4-methylphenyl | NH(CH2)2—O—(CH2)2—SO2—(CH2)2—Cl | yellowish orange |
| 31 | 2,4-disulfo-5-methylphenyl | NH(CH2)3—SO2—(CH2)2—Cl | yellowish orange |
| 32 | 2,4-disulfo-5-methylphenyl | NH(CH2)2—O—(CH2)2—SO2—(CH2)2—Cl | yellowish orange |
| 33 | 2,4-disulfo-5-methylphenyl | N(CH3)—(CH2)2—SO2—(CH2)2—Cl | yellowish orange |
| 34 | 3-methyl-1,6,7-trisulfonaphthyl | NH(CH2)2—SO2—(CH2)2—Cl | yellowish orange |
| 35 | 3-methyl-1,6,7-trisulfonaphthyl | NH(CH2)3—SO2—(CH2)2—Cl | yellowish orange |
| 36 | 3-methyl-1,6,7-trisulfonaphthyl | NH(CH2)2—O—(CH2)2—SO2—(CH2)2—Cl | yellowish orange |
| 37 | 3-methyl-1,6,7-trisulfonaphthyl | N(CH3)—(CH2)2—SO2—(CH2)2—Cl | yellowish orange |
| 38 | 7-methyl-1,3,5-trisulfonaphthyl | NH(CH2)2—SO2—(CH2)2—Cl | yellowish orange |

TABLE 4-continued

| Ex. No. | D | Z | Hue on cotton |
|---|---|---|---|
| 39 | naphthalene with SO₃H, HO₃S, SO₃H, CH₃ | NH(CH₂)₃—SO₂—(CH₂)₂—Cl | yellowish orange |
| 40 | naphthalene with SO₃H, HO₃S, SO₃H, CH₃ | NH(CH₂)₂—O—(CH₂)₂—SO₂—(CH₂)₂—Cl | yellowish orange |
| 41 | naphthalene with SO₃H, HO₃S, SO₃H, CH₃ | N(CH₃)—(CH₂)₂—SO₂—(CH₂)₂—O—Cl | yellowish orange |

EXAMPLE 42 a) 108 g of a salt-containing dye of the formula

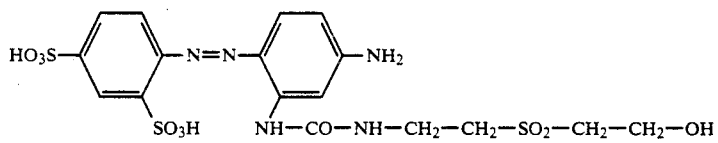

were added to 400 g of sulfuric acid monohydrate at up to an internal temperature of 40° C., and the mixture was subsequently stirred at room temperature for 8 hours. After hydrolysis with 800 ml of ice-water the product was precipitated in acetone. This gave 62.7 g of a compound of the formula

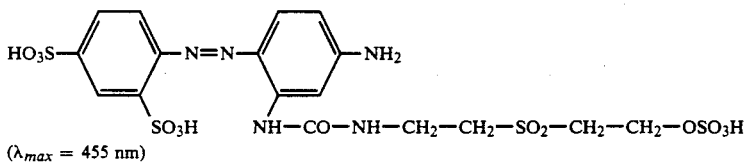

($\lambda_{max}$ = 455 nm)

b) 31.6 g (0.05 mol) of the azo dye described in a) were suspended in 300 ml of water and condensed with equivalent amounts of both cyanuric chloride and N-ethylaniline as described in Example 25.

c) To convert the product into the vinyl sulfone compound, the solution obtained in Example 42b was adjusted at about 30° C. with 2N sodium hydroxide solution until elimination was complete and then neutralized. Potassium chloride was added to salt out a salt-containing dye product which in the form of the free acid conforms to the formula

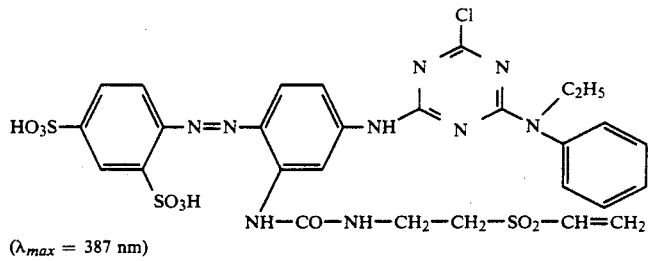

($\lambda_{max}$ = 387 nm)

It dyes cotton in a yellowish orange shade having good fastness properties.

This vinyl compound is also preparable from the dye of Example 26 in an appropriate manner.

(The same method was also used to prepare the vinyl forms of the Examples listed in Tables 3 and 4.)

We claim:
1. A phenylenediamine of the formula II
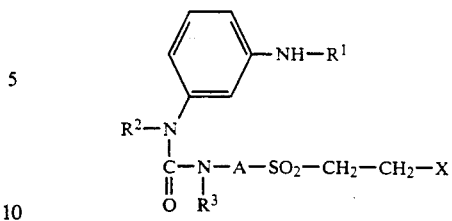
where
R[1], R[2] and R[3] are identical or different and each is independently of the other hydrogen, $C_1$–$C_4$-alkyl or phenyl,
A is $C_2$–$C_8$-alkylene, which may be interrupted by from 1 to 3 oxygen atoms, and X is hydroxyl or halogen.
* * * * *